United States Patent
Ao et al.

(10) Patent No.: US 9,585,831 B2
(45) Date of Patent: *Mar. 7, 2017

(54) COSMETIC COMPOSITION

(71) Applicant: Conopco, Inc., Englewood Cliffs, NJ (US)

(72) Inventors: Mingqi Ao, Shanghai (CN); Naresh Dhirajlal Ghatlia, Shanghai (CN); Hangsheng Li, Shanghai (CN); Qiang Qiu, Trumbull, CT (US); Xiuxia Wang, Shanghai (CN); Caigen Yuan, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/654,564

(22) PCT Filed: Dec. 18, 2013

(86) PCT No.: PCT/CN2013/089837
§ 371 (c)(1),
(2) Date: Jun. 22, 2015

(87) PCT Pub. No.: WO2014/101698
PCT Pub. Date: Jul. 3, 2014

(65) Prior Publication Data
US 2015/0342855 A1     Dec. 3, 2015

(30) Foreign Application Priority Data

Dec. 24, 2012  (WO) ................ PCT/CN2012/087267
Dec. 24, 2012  (WO) ................ PCT/CN2012/087301
Feb. 1, 2013   (EP) ..................................... 13153662
Feb. 1, 2013   (EP) ..................................... 13153664

(51) Int. Cl.
| A61K 8/58 | (2006.01) |
| A61K 8/27 | (2006.01) |
| A61K 8/29 | (2006.01) |
| A61K 8/63 | (2006.01) |
| A61Q 19/08 | (2006.01) |
| A61K 8/892 | (2006.01) |
| A61Q 19/02 | (2006.01) |
| A61K 8/72 | (2006.01) |
| A61K 8/67 | (2006.01) |
| A61K 8/92 | (2006.01) |
| A61Q 19/00 | (2006.01) |
| A61K 8/89 | (2006.01) |
| A61Q 90/00 | (2009.01) |
| A61Q 1/02 | (2006.01) |
| A61K 8/31 | (2006.01) |
| A61K 8/36 | (2006.01) |
| A61K 8/365 | (2006.01) |
| A61K 8/891 | (2006.01) |
| A61K 8/898 | (2006.01) |
| A61K 8/28 | (2006.01) |
| A61Q 17/04 | (2006.01) |

(52) U.S. Cl.
CPC .................. *A61K 8/72* (2013.01); *A61K 8/27* (2013.01); *A61K 8/28* (2013.01); *A61K 8/29* (2013.01); *A61K 8/31* (2013.01); *A61K 8/361* (2013.01); *A61K 8/365* (2013.01); *A61K 8/58* (2013.01); *A61K 8/63* (2013.01); *A61K 8/675* (2013.01); *A61K 8/676* (2013.01); *A61K 8/89* (2013.01); *A61K 8/891* (2013.01); *A61K 8/892* (2013.01); *A61K 8/898* (2013.01); *A61K 8/92* (2013.01); *A61K 8/925* (2013.01); *A61Q 1/02* (2013.01); *A61Q 19/00* (2013.01); *A61Q 19/08* (2013.01); *A61Q 90/00* (2013.01); *A61K 2800/10* (2013.01); *A61K 2800/43* (2013.01); *A61K 2800/54* (2013.01); *A61K 2800/591* (2013.01); *A61K 2800/594* (2013.01); *A61Q 17/04* (2013.01)

(58) Field of Classification Search
None
See application file for complete search history.

(56) References Cited

U.S. PATENT DOCUMENTS

| 5,599,547 A | 2/1997 | Bartholomey et al. |
| 6,074,652 A | 6/2000 | Ishiwatari et al. |
| 2001/0003586 A1 | 6/2001 | Vatter et al. |
| 2003/0031637 A1 | 2/2003 | Loginova et al. |

(Continued)

FOREIGN PATENT DOCUMENTS

| EP | 1716888 | 11/2006 |
| EP | 1772138 | 4/2007 |

(Continued)

OTHER PUBLICATIONS

PDMS (polydimethylsiloxane) MSDS: ([retrieved from on-line website: http://www.mit.edu/~6.777/matprops/pdms.htm, last visit Jan. 28, 2016]).*
Klykken, "Silicone Film-Forming Technologies for health care applications", Dow Corning, pp. 1-8 (2009).*
Beewax m.p., Wikipedia: [https://en.wikipedia.org/wiki/Beeswax, last visit Jan. 27, 2016].*
Paraffin wax m.p., Wikipedia: [https://en.wikipedia.org/wiki/Paraffin_wax, last visit Jan. 27, 2016].*
Ceresin wax m.p., Freedictionary ([http://encyclopedia2.thefreedictionary.com/Ceresin, last visit Jan. 28, 2016]).*
IPRP in PCTCN2013089848, May 5, 2015.
IPRP2 in PCTCN2013089837, Jun. 10, 2015.
IPRP2 in PCTCN2013089863, May 6, 2015.

(Continued)

*Primary Examiner* — Ernst V Arnold
*Assistant Examiner* — Kyung Sook Chang
(74) *Attorney, Agent, or Firm* — Edward A. Squillante, Jr.

(57) ABSTRACT

Disclosed is a cosmetic composition comprising a first film-forming polymer having a contact angle of at least 85°, a second film-forming polymer having a contact angle of at least 85°, a lipid having a melting point of at least 5° C., optical particle, and at least 20% of water by weight of the composition.

20 Claims, No Drawings

(56) References Cited

U.S. PATENT DOCUMENTS

| | | |
|---|---|---|
| 2003/0232030 A1 | 12/2003 | Lu et al. |
| 2005/0089498 A1* | 4/2005 | Patil ................. A61K 8/891 424/70.122 |
| 2006/0127333 A1 | 6/2006 | Patil et al. |
| 2006/0292096 A1 | 12/2006 | Yu |
| 2007/0093619 A1 | 4/2007 | Bui et al. |
| 2007/0166271 A1* | 7/2007 | Gordon ............... A61K 8/585 424/70.122 |
| 2007/0243143 A1 | 10/2007 | Patil et al. |
| 2008/0233075 A1 | 9/2008 | Sokolinsky et al. |
| 2008/0292560 A1 | 11/2008 | Tamarkin et al. |
| 2009/0214458 A1 | 8/2009 | Brun |
| 2011/0236332 A1 | 9/2011 | Dop |
| 2012/0064020 A1 | 3/2012 | Gempler et al. |
| 2012/0121673 A1 | 5/2012 | Susak et al. |
| 2013/0071341 A1 | 3/2013 | Ishida |
| 2013/0295028 A1 | 11/2013 | Lee et al. |
| 2014/0213750 A1 | 7/2014 | Brandstadt et al. |

FOREIGN PATENT DOCUMENTS

| | | |
|---|---|---|
| EP | 2263639 | 12/2010 |
| FR | 2918272 | 1/2009 |
| FR | 2958544 | 10/2011 |
| JP | 2004203788 | 7/2004 |
| JP | 2005263699 | 9/2005 |
| JP | 2009167145 | 7/2009 |
| JP | 2010144025 | 7/2010 |
| JP | 2012077049 | 4/2012 |
| KR | 20080086620 | 9/2008 |
| WO | WO0117496 | 3/2001 |
| WO | WO03026596 | 4/2003 |
| WO | WO2005060923 | 7/2005 |
| WO | WO2005107691 | 11/2005 |
| WO | WO2009016555 | 2/2009 |
| WO | WO2010129445 | 11/2010 |
| WO | WO2010149493 | 12/2010 |
| WO | WO2011117976 | 9/2011 |
| WO | WO2011145053 | 11/2011 |
| WO | WO2011148328 | 12/2011 |
| WO | WO2012079873 | 6/2012 |
| WO | WO2013102065 | 7/2013 |

OTHER PUBLICATIONS

IPRP2 in PCTCN2013089870, May 4, 2015.
Search Report in PCTCN2013089837, Mar. 27, 2014.
Search Report in PCTCN2013089848, Mar. 27, 2014.
Search Report in PCTCN2013089863, Mar. 20, 2014.
Search Report in PCTCN2013089870, Mar. 27, 2014.
Written Opinion in PCTCN2013089837, Mar. 27, 2014.
Written Opinion in PCTCN2013089848, Mar. 27, 2014.
Written Opinion in PCTCN2013089863, Mar. 20, 2014.
Written Opinion in PCTCN2013089870, Mar. 27, 2014.
Dow Corning Product Information Personal Care "Dow Corning MQ-1640 Flake Resin", 2012, pp. 1-3.
Co-Pending Appln., filed Jun. 22, 2015; Entitled: Cosmemtic Composition.
Co-Pending Appln., filed Jun. 22, 2015; Entitled: Cosmetic Composition.
Search Report in EP13869168, Sep. 30, 2015.
Written Opinion in EP13869168, Sep. 30, 2015.
Search Report in EP13868581, Dec. 16, 2015.
Written Opinion in EP13868581, Dec. 16, 2015.
Search Report and Written Opinion in EP13869125, Feb. 3, 2016.

* cited by examiner

COSMETIC COMPOSITION

FIELD OF THE INVENTION

The present invention relates to a cosmetic composition. Particularly, the present invention relates to a cosmetic composition comprising a first film-forming polymer having a contact angle of at least 85°, a second film-forming polymer having a contact angle of at least 85°, a lipid having a melting point of at least 5° C., optical particle, and at least 20% of water by weight of the composition.

BACKGROUND OF THE INVENTION

Usually, consumers have some skin problems including dryness, wrinkles and fine lines, loose/saggy skin and age spots. Composition comprising film-forming polymer may be one solution for consumers to these problems. Film-forming polymer would form a film onto the skin after applying topically and bring immediate firming effect to the skin. Some beneficial agents, for example optical particle and sunscreen agent, may also be delivered onto skin surface together with the film-forming polymer.

There is an increasing interest to develop a skin care composition comprising a film-forming polymer.

US patent application with publication number of US 2008/0233075 A1 disclosed a topical composition comprising a water-soluble film-forming polymer, a bimodal copolymer comprising a first polymeric component with anionic functional groups and a second polymeric component with cationic functional groups, and one or more biological polymers that are derived from a source selected from the group consisting of animals, plants, algae, fungi, and bacteria or are biotechnologically synthesized. Such a topical composition was said to be applied to saggy or wrinkled skin for enhancing the appearance of the skin.

However, after applying cosmetic composition, the skin may undergo water washing and abrasion by hand and therefore the film formed by film-forming polymer on the skin may be easily washed away and/or rubbed away and therefore lose the benefits. Meanwhile, the beneficial agent would be easily washed off and/or rubbed off and thus can not provide a long-lasting benefit.

Therefore, the present inventors have recognized a need to develop a cosmetic composition with improved wash-off resistance, abrasion resistance, and/or long-lasting deposition of beneficial agent. Therefore, this invention is directed to a cosmetic composition a first film-forming polymer having a contact angle of at least 85°, a second film-forming polymer having a contact angle of at least 85°, a lipid having a melting point of at least 5° C., optical particle, and at least 20% of water by weight of the composition.

SUMMARY OF THE INVENTION

In a first aspect, the present invention is directed to a cosmetic composition comprising a first film-forming polymer having a contact angle of at least 85°, a second film-forming polymer having a contact angle of at least 85°, a lipid having a melting point of at least 5° C., optical particle, and at least 20% of water by weight of the composition.

In a second aspect, the present invention is directed to a method for improving skin characteristic comprising the step of topically applying to skin any embodiment of the first aspect.

In a third aspect, the present invention is directed to use of any embodiment of the first aspect for improving any attribute selected from opacity, long-lasting opacity, cumulative deposition of optical particle, wash-off resistance, abrasion resistance, or combination thereof.

All other aspects of the present invention will more readily become apparent upon considering the detailed description and examples which follow.

DETAILED DESCRIPTION OF THE INVENTION

Except in the examples, or where otherwise explicitly indicated, all numbers in this description indicating amounts of material or conditions of reaction, physical properties of materials and/or use may optionally be understood as modified by the word "about".

All amounts are by weight of the composition, unless otherwise specified.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Film-forming polymer" as used herein refers to polymer which is capable of forming cohesive and continuous covering over the hair and/or skin when applied to their surface.

"Silicone resin" as used herein refers to silicone material which is formed by branched, and/or cage-like oligosiloxanes having three-dimensional structure. Typically, the silicone resin is rigid.

"Lipid" as used herein refers to a class of naturally occurring organic compounds or their analogues which is insoluble in water. Insoluble in water refers to compound that dissolves in water to give a solution with a concentration of less than 5% by weight of the solution, preferably less than 1% and more preferably less than 0.1% by weight of the solution. Typically, the lipid includes fatty acid, soap, fatty ester, wax, fatty alcohol, phospholipid, eicosonoid, terpene, steroid, ceramide, and lipid-soluble vitamins.

"Fatty compound" refers organic compound having a straight-chain with length of at least 8 carbon atoms, preferably at least 10 carbon atoms. More preferably, the fatty compound has a $C_{10}$ to $C_{36}$ straight-chain, even more preferably a $C_{12}$ to $C_{28}$ straight-chain.

"Wax" as used herein refers to a class of organic compounds that characteristically comprise long alkyl chains. Typically the waxes are plastic (malleable) at about 25° C.

"Wax ester" as used herein means ester which is comprised by a wax.

"Contact angle" (CA), as used herein, means the angle at which a water/vapor interface meets a solid surface at a temperature of 25° C. Such an angle may be measured with a goniometer or other water droplet shape analysis systems with water droplet of 5 µl and at 25° C.

"Melting point" as used herein is the temperature at which it changes state from solid to liquid at atmospheric pressure. When referring to the melting point of wax, it means the temperature at which the wax began to soften. The melting point of lipid other than wax may be measured for example by method in standard of ISO 6321-2002. The melting point of wax may be measured for example by method in standard of ISO 6244-1982 or by Differential Scanning Calorimetry (DSC) but preferably by method in standard of ISO 6244-1982.

"Optical particle" refers to particle which can impart opacity to skin. Opacity as used herein will also include masking/reducing blemishes, even skin tone and/or skin lightening. "Refractive index values" referred to herein are those determined at a temperature of 25° C. and a wavelength of 589 nm unless otherwise stated.

"Leave-on" as used with reference to compositions herein means a composition that is applied to or rubbed on the skin, and left thereon. 'Wash-off' as used with reference to compositions herein means a skin cleanser that is applied to or rubbed on the skin and rinsed off substantially immediately subsequent to application. "Skin" as used herein includes the skin on the face (except eye lids and lips), neck, chest, abdomen, back, arms, underarm area, hands, and legs. Preferably "skin" means skin on the face except eye lids and lips. More preferably, "skin" means skin on cheeks.

In some preferred embodiments, the composition is neither a cosmetic composition comprising silicone resin, non-volatile silicone oil, and cosmetically acceptable carrier, wherein the non-volatile silicone oil comprises dimethiconol, aminosilicone or a mixture thereof and the weight ratio of the silicone resin to the non-volatile silicone oil is at least 1:4; nor a cosmetic composition comprising a silicone resin, a steroid, and cosmetically acceptable carrier, wherein the weight ratio of silicone resin to steroid is at least 5:9.

The requirement for the film-forming polymers of the present invention is that the film-forming polymer is suitable for use in cosmetic composition and the first film-forming polymer is different from the second film-forming polymer. For better performance of wash-off resistance, at least one film-forming polymer preferably has a contact angle of at least 90°, more preferably from 95° to 160°, most preferably from 100° to 120°. In more preferred embodiments, both of the two film-forming polymers have a contact angle of at least 90°, even more preferably from 95° to 160°, most preferably from 100° to 120°.

The first and/or second film-forming polymer may for example comprise silicone resin, chitosan, polyurethane, polyvinyl butyral resin, or a mixture thereof. More preferably, the first and/or second film-forming polymer comprises silicone resin, more preferably both the first and second film-forming polymers comprise silicone resin and most preferably both the first and second film-forming polymers are silicone resins.

The silicone resin is typically described by the following siloxy monomeric units:

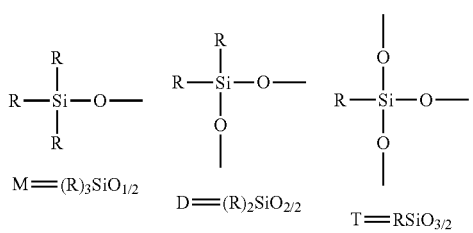

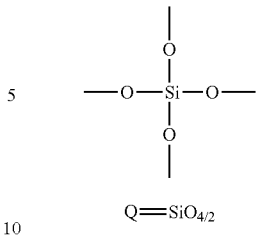

The R group may be selected from saturated or unsaturated hydrocarbon groups. Preferably, the silicone resin of the present invention may be selected from siloxysilicate, silsesquioxane, or a mixture thereof. More preferably, the silicone resin comprises M unit, Q unit, T unit or combination thereof. Even more preferably, the silicone resin comprises MQ silicone resin, T silicone resin, or a mixture thereof.

Preferably, the first film-forming polymer comprises MQ silicone resin, more preferably is MQ silicone resin. The second film-forming polymer preferably comprises T silicone resin, more preferably is a T silicone resin.

Preferably, the MQ silicone resin has the formula of $[(R_1)_3-Si-O_{1/2}]_a-(Si-O_{4/2})_b$, wherein $R_1$ is mutually identical or different, selected from saturated hydrocarbon groups. $R_1$ is preferably selected from $C_1$ to $C_6$ alkyl, and more preferably each $R_1$ is methyl group. Thus, the more preferred MQ silicone resin is trimethylsiloxysilicate. Preferably, a and b independently have values ranging from 10 to 1000, and more preferably from 30 to 200.

Preferably, the T silicone resin has the formula of $[R_2-Si-O_{3/2}]_x$, wherein $R_2$ is selected from saturated hydrocarbon groups. $R_2$ is preferably selected from $C_1$ to $C_6$ alkyl, more preferably selected from methyl, ethyl, propyl, butyl, and most preferably propyl. The most preferred T silicone resin is polypropyl silsesquioxane. Preferably, x is less than 2000, more preferably less than 500, but preferably greater than 10, and more preferably greater than 50.

In more preferred embodiments, the first and the second film-forming polymers are a blend of MQ silicone resin and T silicone resin. The weight ratio of the MQ silicone resin to the T silicone resin is preferably from 1:20 to 20:1 in order to achieve better film-forming performance. More preferably, the weight ratio of the MQ silicone resin to the T silicone resin is from 1:10 to 10:1, even more preferably from 1:5 to 5:1. Exemplary blend of MQ and T Propyl resin suitable for the present invention includes Dow Corning™ MQ-1640 Flake Resin.

Preferably, the total amounts of the two film-forming polymers is 0.01 to 20% by weight of the composition, more preferably from 0.2 to 10%, even more preferably from 0.5 to 7%, and most preferably from 1 to 4% by weight of the composition. The weight ratio of the first film-forming polymer to the second film-forming polymer is typically in the range of from 50:1 to 1:20, more preferably from 20:1 to 1:10, even more preferably from 6:1 to 1:2, and most preferably from 4:1 to 1:1.

Without wishing to be bound to any theory or explanation, the present inventors believe that the lipid was embedded into the network of film-forming polymer layer to form a compact film. Such film has stronger binding force to the substrates and improved the performance of wash-off resistance. Therefore, to form a stronger film and/or be better compatible with the film-forming polymer, the lipid preferably has a melting point of at least 10° C., more preferably at least 35° C., even more preferably from 40° C. to 200° C., and most preferably from 50° C. to 150° C.

Preferably, the lipid comprises fatty acid, soap, fatty alcohol, fatty ester, wax, steroid, ceramide, or a mixture thereof, more preferably the lipid comprises fatty acid, soap, wax, steroid, ceramide or a mixture thereof, even more preferably the lipid comprises fatty acid, soap, wax, steroid or a mixture thereof and most preferably the lipid comprise fatty acid, soap, wax, or a mixture thereof.

In certain embodiments, the lipid preferably comprises fatty compound, more preferably is fatty compound. The fatty compound typically comprises fatty acid, soap, wax, fatty alcohol, fatty ester or a combination thereof. More preferably the fatty compound is selected from fatty acid, soap, wax, or a combination thereof.

The lipid is preferably present in the composition in amount of from 0.01 to 20% by weight of the composition, more preferably from 0.1 to 10%, even more preferably from 0.2 to 5%, and most preferably from 0.5 to 3% by weight of the composition.

For better performance of wash-off resistance, and/or long-lasting opacity, the weight ratio of film-forming polymer to the lipid is preferably from 1:10 to 50:1, more preferably from 1:2 to 10:1, even more preferably from 1:1 to 5:1, and most preferably from 2:1 to 4:1.

In certain embodiments, the weight ratio of the total film-forming polymers to the lipid is preferably at least 5:9, more preferably from 3:2 to 35:1, more preferably still from 9:4 to 20:1 even more preferably from 5:2 to 8:1 and most preferably from 8:3 to 5:1.

The fatty acid typically contains fatty acid moieties with chain lengths of from C10 to C30. In certain preferred embodiments, the hydrocarbon chain length of the fatty acid used is from 12 to 24, more preferably 14 to 20, even more preferably 16 to 18 carbon atoms. Suitable fatty acid comprises pelargonic, lauric, myristic, palmitic, isopalmitic, stearic, isostearic, oleic, linoleic, ricinoleic, arachidic, behenic, erucic acid or a mixture thereof. More preferably, the fatty acid comprises stearic, lauric, palmitic, isostearic, myristic acid, or a mixture thereof. Even more preferably, the fatty acid is stearic acid, palmitic acid or a mixture thereof.

Although normally saturated, suitable fatty acid may contain unsaturated fatty acid moieties, and may contain fatty acid moieties having a degree of substitution, such as e.g. hydroxy fatty acids. It is preferred that the fatty acid comprises saturated fatty acid, saturated fatty acid having a degree of substitution, or a combination thereof. More preferably, the fatty acid comprises saturated is selected from saturated fatty acid, saturated fatty acid having a degree of substitution, or a combination thereof. Even more preferably, the fatty acid is saturated fatty acid.

Soap of the present invention is preferably a salt of a $C_{10}$-$C_{30}$ fatty acid, more preferably $C_{12}$-$C_{24}$ fatty acid, even more preferably $C_{14}$-$C_{20}$ fatty acid and most preferably $C_{16}$-$C_{18}$ fatty acid. Suitable soap comprises pelargonate, laurate, myristate, palmitate, stearate, isostearate, oleate, linoleate, ricinoleate, arachidate, behenate, erucate salt or a mixture thereof. More preferably, the fatty acid salt comprises stearate, laurate, palmitate, isostearate salt or a mixture thereof. Even more preferably, the fatty acid salt is stearate salt, palmitate salt or a mixture thereof.

Preferably the soap is selected from ammonium salt, alkali metal salt or mixture thereof. More preferably, the soap is sodium and/or potassium salt, and most preferably sodium salt. When the lipid comprises fatty acid and soap, it is preferred the lipid comprises fatty acid and salt thereof. More preferably the lipid is a combination of fatty acid and salt thereof.

The requirement of wax is that the wax may be applicable in cosmetic composition. The wax may be natural wax and/or synthetic wax. Such waxes are often selected from hydrocarbon waxes and ester waxes but the wax preferably comprises wax ester. In some preferred embodiments, the wax comprises beeswax, rice bran wax, montan wax, spermaceti wax, carnauba wax, candelilla wax, sugarcane wax, insect wax, petroleum jelly, or a mixture thereof. More preferably, the wax comprises beeswax, rice bran wax, montan wax, carnauba wax, petroleum jelly or a mixture thereof. Even more preferably, the wax is selected from beeswax, petroleum jelly or a mixture thereof. Most preferably, the wax is beeswax. For example, the waxes suitable for use in this invention include beeswax from Koster Keunen Inc.

Representative fatty alcohols comprise from 8 to 40 carbon atoms, more preferably 10 to 32, even more preferably from 12 to 26 and most preferably from 16 to 22. Examples of suitable fatty alcohols include myristyl, pentadecyl, cetyl, stearyl, behenyl and mixtures thereof. More preferably the fatty alcohol is selected from cetyl alcohol, stearyl alcohol, or a mixture thereof.

Fatty ester preferably is the ester of saturated fatty acid having 10 to 30 carbon atoms. Exemplary fatty ester suitable for the present invention includes alkenyl or alkyl esters of fatty acid, preferably having 10 to 24 carbon atoms; ether-esters such as fatty acid esters of ethoxylated saturated fatty alcohols; polyhydric alcohol esters particularly ethylene glycol mono- and di-fatty acid esters, diethylene glycol mono- and di-fatty acid esters.

There is no particular limitation regarding to the steroid of the present invention provided that the steroid is suitable to use in cosmetic composition. Preferably, the steroid comprises hydroxyl group, more preferably comprise a sterol and even more preferably the steroid is a sterol. The sterol may comprise phytosterol, zoosterol, fungi sterol, or a mixture thereof. It is preferred that the sterol comprise zoosterol.

Exemplary sterol includes cholesterol, 3-sitosterol, stigmasterol, campesterol, brassicasterol, ergosterol, cholestanol, cholestenone, 7-ketocholesterol, 5α,6α-epoxycholestanol, 5β,6β epoxycholestanol, and 7-dehydrocholesterol, 15-ketocholestene, 15-ketocholestane, 25-hydroxycholesterol, 27-hydroxycholesterol, 24-hydroxycholesterol, 24,25-epoxycholesterol, 24-dihydrolanosterol, lanosterol, or a mixture thereof.

It is preferred that the sterol comprises cholesterol, oxysterol, or a mixture thereof. More preferably the sterol comprises cholesterol. The sterol preferably comprises at least 30% of cholesterol by weight of the sterol, more preferably at least 50% by weight, and even more preferably from 80 to 100% by weight of the sterol. Most preferably, the sterol is cholesterol.

When the composition comprises steroid, the steroid is preferably present in the composition in amount of from 0.01 to 10% by weight of the composition, more preferably from 0.05 to 5%, even more preferably from 0.1 to 3%, and most preferably from 0.3 to 1.5% by weight of the composition.

When the composition comprises silicone resin and steroid, the weight ratio of silicone resin to steroid is at least 5:9. For better performance of wash-off resistance, abrasion resistance and/or long-lasting benefits of beneficial agent, the weight ratio of silicone resin to steroid is preferably from 5:7 to 50:1, more preferably from 3:2 to 35:1, more preferably still from 9:4 to 20:1 even more preferably from 5:2 to 8:1 and most preferably from 8:3 to 5:1.

The cosmetic composition also comprises optical particle. Without being bound to any particular theory or explanation, the present inventor believe that optical particles would be embedded into the film by film-forming polymer and wax. Therefore, the optical particles are able to resistant water and/or friction and deliver the long-lasting opacity to the skin.

The optical particles are typically particles of high refractive index materials. For example the optical particles may have a refractive index of greater than 1.3, more preferably greater than 1.7 and most preferably from 2.0 to 2.7. Examples of such optical particles are those comprising bismuth oxy-chloride, boron nitride, barium sulfate, mica, silica, titanium dioxide, zirconium oxide, iron oxide, aluminium oxide, zinc oxide or combinations thereof. More preferred particles are particles comprising titanium dioxide, zinc oxide, zirconium oxide, mica, iron oxide or a combination thereof. Even more preferred particles are particles comprising zinc oxide, zirconium oxide, titanium dioxide or a combination thereof as these materials have especially high refractive index. Most preferred is titanium dioxide.

For sake of good compatibility with the film-forming polymer and/or wax, the optical particle is preferably hydrophobic. More preferably, the optical particle is preferably hydrophobically modified. Even more preferably the optical particle is modified by hydrophobic material selected from fatty acid, silicone oil, wax, and a mixture thereof. The fatty acid preferably comprises oleic acid, stearic acid, or a mixture thereof.

The size of optical particle is typical from 2 nm to 5 microns, more preferably from 5 nm to 1 micron, even more preferably from 10 nm to 500 nm. Particle size as used herein refers to the diameter of particles in an unaggregated state. Diameter means the largest measurable distance on a particle in the event a well-defined sphere is not generated. The diameter may be measured for example by scanning electron microscopy (SEM) by averaging the value of at least ten particles.

Preferably the composition comprises optical particles in an amount of from 0.001 to 10 wt %, more preferably 0.01 to 7 wt %, more preferably still 0.05 to 5 wt % and most preferably 0.1 to 2 wt %. The weight ratio of the total amounts of film-forming polymers to the optical particle is preferably in the range of from 1:10 to 50:1, more preferably from 1:3 to 10:1, and most preferably from 1:1 to 5:1. The weight ratio of the lipid to the optical particle is preferably in the range of from 1:40 to 20:1, more preferably from 1:20 to 10:1, and most preferably from 1:10 to 5:1.

Compositions of the present invention will also include at least 20% of water by weight of the composition. Preferably, the amounts of water is at least 40%, more preferably range from more preferably from 50 to 90%, optimally between 60 and 85% by weight of the composition.

Emollient materials may be included as carriers in compositions of this invention. These may be in the form of silicone oils, synthetic esters and/or hydrocarbons. Amounts of the emollients may range, for example, anywhere from 0.1 to 95%, more preferably between 1 and 50% by weight of the composition.

Silicone oils may be divided into the volatile and nonvolatile variety. The term "volatile" as used herein refers to those materials which have a measurable vapor pressure at ambient temperature (25° C.). Volatile silicone oils are preferably chosen from cyclic (cyclomethicone) or linear polydimethylsiloxanes containing from 3 to 9, preferably from 4 to 5, silicon atoms. In many liquid versions of compositions according to the present invention, the volatile silicone oils may form a relatively large component of the compositions as carriers. Amounts may range, for example, from 5% to 80%, more preferably from 20% to 70% by weight of the composition.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 m$^2$/s at 25° C. Among the preferred nonvolatile emollients useful in the present compositions are the polydimethyl siloxanes having viscosities from about $1 \times 10^{-5}$ to about $4 \times 10^4$ m$^2$/s at 25° C.

Organopolysiloxane crosspolymers can be usefully employed. Representative of these materials are dimethicone/vinyl dimethicone crosspolymers and dimethicone crosspolymers available from a variety of suppliers including Dow Corning (9040, 9041, 9045, 9506 and 9509), General Electric (SFE 839), Shin Etsu (KSG-15, 16 and 18 [dimethicone/phenyl vinyl dimethicone crosspolymer]), and Grant Industries (Gransil brand of materials), and lauryl dimethicone/vinyl dimethicone crosspolymers supplied by Shin Etsu (e.g. KSG-31, KSG-32, KSG-41, KSG-42, KSG-43 and KSG-44). Amounts of the aforementioned organopolysiloxane crosspolymers (when present) will usually be from 0.1 to 20% by weight dissolved usually in a volatile silicone oil such as cyclomethicone.

When silicones are present in large amounts as carrier and water is also present, the systems may be oil continuous. These normally will require emulsification with a water-in-oil emulsifier such as a dimethicone copolyol (e.g. Abil EM-90 which is cetyl dimethicone copolyol).

Among the ester emollients are:
a) Alkenyl or alkyl esters of fatty acids having 10 to 20 carbon atoms. Examples thereof include isoarachidyl neopentanoate, isodecyl neopentanoate, isopropyl myristate, isononyl isonanoate, cetyl ricinoleate, oleyl myristate, oleyl stearate, and oleyl oleate.
b) Ether-esters such as fatty acid esters of ethoxylated fatty alcohols.
c) Polyhydric alcohol esters. Butylene glycol, ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols. Exemplative is pentaerythrityl tetraethylhexanoate.
d) Wax esters such as beeswax, spermaceti wax and tribehenin wax.
e) Sterols esters, of which cholesterol fatty acid esters are examples thereof.
f) Sugar ester of fatty acids such as sucrose polybehenate and sucrose polycottonseedate.

Of particular use also are the $C_{12-15}$ alkyl benzoate esters sold under the Finsolv brand.

Hydrocarbons which are suitable cosmetically acceptable carriers include petrolatum, mineral oil, $C_{11}$-$C_{13}$ isoparaffins, polyalphaolefins, and especially isohexadecane, available commercially as Permethyl 101A from Presperse Inc.

Humectants of the polyhydric alcohol-type can be employed as cosmetically acceptable carriers. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, glycerol, ethoxylated glycerol, propoxylated glycerol and mixtures thereof. The amount of humectant may range, for example, anywhere from 0.5 to 50%, more preferably between 1 and 15% by weight of the composition. Most preferred is glycerol (also known as glycerin). Amounts of glycerin may range, for example, from 1% to 50%, more preferably from 10 to 35%, optimally from 15 to 30% by weight of the composition.

Besides optical particles, the compositions of this invention may include a variety of other functional ingredients. Sunscreen actives may be included in compositions of the present invention. These will be organic compounds having at least one chromophoric group absorbing within the ultraviolet ranging from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-isopropyldibenzoylmethane; Butylmethoxydibenzoylmethane; Etocrylene; and 4-isopropyl-dibenzoylmethane). Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Particularly preferred are such materials as ethylhexyl p-methoxycinnamate, available as Parsol MCX®, Avobenzone, available as Parsol 1789®, Dermablock OS® (octylsalicylate) and Mexoryl SX® (with INCI name of Terephthalylidene Dicamphor Sulfonic Acid).

Amounts of the organic sunscreen agent may range, for example, from 0.1 to 15%, more preferably from 0.5% to 10%, optimally from 1% to 8% by weight of the composition.

A variety of thickening agents may be included in the compositions. Illustrative but not limiting are stearic acid, Acrylamide/Sodium Acryloyldimethyltaurate Copolymer (Aristoflex AVC), Hydroxyethyl Acrylate/Sodium Acryloyldimethyltaurate Copolymer, Aluminum Starch Octenyl Succinate, Polyacrylates (such as Carbomers including Carbopol® 980, Carbopol® 1342, Pemulen TR-2® and the Ultrez® thickeners), Polysaccharides (including xanthan gum, guar gum, pectin, carageenan and sclerotium gums), celluloses (including carboxymethyl cellulose, ethyl cellulose, hydroxyethyl cellulose and methyl hydroxymethyl cellulose), minerals (including talc, silica, alumina, mica and clays, the latter being represented by bentonites, hectorites and attapulgites), magnesium aluminum silicate and mixtures thereof. Amounts of the thickeners may range, for example, from 0.05 to 10%, more preferably from 0.3 to 2% by weight of the composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, butyl paraben, isobutyl paraben, imidazolidinyl urea, sodium dehydroacetate and benzyl alcohol. The preservatives should be selected having regard for the use of the composition and possible incompatibilities between the preservatives and other ingredients in the composition. Preservatives are preferably employed in amounts ranging from 0.01% to 2% by weight of the composition.

Compositions of the present invention may also contain vitamins and flavonoids. Illustrative water-soluble vitamins are Niacinamide, Vitamin $B_2$, Vitamin $B_6$, Vitamin C, ascorbyl phosphate and Biotin. Among the useful water-insoluble vitamins are Vitamin A (retinol), Vitamin A Palmitate, ascorbyl tetraisopalmitate, Vitamin E (tocopherol), Vitamin E Acetate and DL-panthenol. A particularly suitable Vitamin $B_6$ derivative is Pyridoxine Palmitate. Among the preferred flavonoids are glucosyl hesperidin and rutin. Total amount of vitamins or flavonoids when present in compositions according to the present invention may range, for example, from 0.001 to 10%, more preferably from 0.01% to 5%, optimally from 0.1 to 3% by weight of the composition.

Desquamation agents are further optional components. Illustrative are the alpha-hydroxycarboxylic acids and beta-hydroxycarboxylic acids and salts of these acids. Among the former are salts of glycolic acid, lactic acid and malic acid. Salicylic acid is representative of the beta-hydroxycarboxylic acids. Amounts of these materials when present may range from 0.1 to 15% by weight of the composition.

A variety of herbal extracts may optionally be included in compositions of this invention. Illustrative are pomegranate, white birch (*Betula Alba*), green tea, chamomile, licorice, *boswellia serrata*, olive (*Olea Europaea*) leaf, *arnica montana* flower, *lavandula angustifolia*, and extract combinations thereof. The extracts may either be water soluble or water-insoluble carried in a solvent which respectively is hydrophilic or hydrophobic. Water and ethanol are the preferred extract solvents.

Miscellaneous other adjunct cosmetic ingredients that may be suitable for the present compositions include ceramides (e.g. Ceramide 3 and Ceramide 6), conjugated linoleic acids, colorants (e.g. iron oxides), metal (manganese, copper and/or zinc) gluconates, allantoin, palmitoyl pentapeptide-3, amino acids (e.g. alanine, arginine, glycine, lysine, proline, serine, threonine, glumatic acid and mixtures thereof), trimethylglycine, sodium PCA, chelator like disodium EDTA, magnesium aspartate, and combinations thereof. Amounts may, for example, vary from 0.000001 to 3% by weight of the composition.

A small amount of emulsifying surfactant may be present. Surfactants may be anionic, nonionic, cationic, amphoteric and mixtures thereof. Levels may range, for example, from 0.1 to 5%, more preferably from 0.1 to 2%, optimally from 0.1 to 1% by weight. Advantageously the amount of surfactant present should not be sufficient for lather formation. In these instances, less than 2% by weight, preferably less than 1%, and optimally less than 0.5% by weight surfactant is present. Emulsifiers like PEG-100 stearate may be used as well as emulsion stabilizers like cetearyl alcohol and ceteareth-20 may be used and typically in amounts that do not exceed 5 percent by weight of the composition.

Other optional additives suitable for use in the composition of this invention include cationic ammonium compounds to enhance moisturization. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyl tri($C_1$-$C_3$ alkyl or hydroxyalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from 0.01 to 30%, and more preferably from about 0.1 to about 15% by weight of the composition.

When cationic ammonium compounds are used, optional additives for use with the same are moisturizing agents such as substituted ureas like hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-di-hydroxyethyl urea; N,N'-dihydroxypropyl urea; N,N,N'-tri-hydroxyethyl urea; tetra(hydroxymethyl) urea; tetra(hydroxyethyl) urea; tetra(hydroxypropyl) urea; N-methyl-N'-hydroxyethyl urea; N-ethyl-N'-hydroxyethyl urea; N-hydroxypropyl-N'-hydroxyethyl urea and N,N'dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from AkzoNobel under the trademark Hydrovance. Such substituted ureas, while desirable in moisturizing formulations, are only selected for use when compatible with sunless tanning agent or agents (when used) in the compositions of this invention.

Amounts of substituted urea, when used, in the composition of this invention range from 0.01 to 20%, more preferably from 0.5 to 15%, and most preferably from 2 to 10% based on total weight of the composition and including all ranges subsumed therein.

When cationic ammonium compound and substituted urea are used, in a most especially preferred embodiment at least from 0.01 to 25%, more preferably from 0.2 to 20%, and most preferably from 1 to 15% humectant, like glycerine, is used, based on total weight of the composition and including all ranges subsumed therein.

When making the compositions of this invention, ingredients are typically mixed with moderate shear under atmospheric conditions. The compositions may be applied topically and preferably 1-4 milligrams of composition is applied per square centimeter of skin. Preferably, the compositions display a pH from 5 to 7. Packaging for the composition of this invention can be a jar or tube as well as any other format typically seen for cosmetic, cream, washing and lotion type products.

It is preferred that the composition is a skin care composition. The composition may be a leave-on composition or a wash-off composition, but preferably a leave-on composition.

The invention also concerns a method for improving skin characteristic comprising the step of topically applying to skin the cosmetic composition of the invention as described. Skin characteristic as used herein refers to features used to evaluate skin, include but not limit to skin firming, opacity, smoothness, cleanliness, moistening, or a combination thereof. Preferably, the skin characteristics comprise skin firming, opacity, or a combination thereof. More preferably the skin characteristic is long-lasting opacity and most preferably, the skin characteristic is long-lasting whitening. "Long-lasting" refers to the beneficial agent (for example optical particle) remains at least 30%, preferably at least 50% after flushing by tap water (25° C.) for 1 minute.

The following examples are provided to facilitate an understanding of the invention. The examples are not intended to limit the scope of the claims.

EXAMPLES

Wash-Off/Abrasion Resistance Test

1. Constructing a Calibration Curve

The base formulation (sample A in Table 1) was coated evenly onto Bio-skin plate (Color: 30#, ex. BEAULAX, Co. Ltd., Tokyo, Japan) with surface density of 0, 0.5, 1, 1.5, 2, 2.5, 3, 3.5, 4, 5, and 6 mg/cm². After naturally drying at around 25° C. for 8 hours, the L (for lightness), a, and b (for the color-opponent dimensions) of these coated Bio-skin plates was measured using Digieye Imaging System (Verivide, UK). The ITA value was calculated by equation of ITA=[arctan(L−50/b)]×180/π. Then the ITA value versus surface density was plotted and fitted by a polynomial model to obtain the curve. The R-Square was higher than 0.999 which demonstrated that the polynomial model was suitable to fit the functional relationship between the lightness and the surface density of the base formulation.

2. Wash-Off/Abrasion Experiment 30 mg of samples was coated evenly onto Bio-skin plates with area of 10 cm². The coated bio-skin was naturally dried at around 25° C. for 8 hours. The L, a and b of the Bio-skin plate were measured by Digieye Imaging System (Verivide, UK). The ITA value (ITA$_1$) was calculated according to the above equation. The surface density value before wash-off/abrasion experiment (SD$_1$) was obtained according to the calibration curve. The coated bio-skin was soaked into de-ionized water for 30 s. Then, a commercial face cleanser (Pond's gold Radiance™ Radiance Boosting Cleansing Mousse) with amount of 5 mg/cm$^2$ was applied onto the Bio-skin plate and the coated Bio-skin plate was washed by Martindale abrasion and pilling tester (Type: M235, SDL Altas, USA) with 33.72 g of motion plate at the speed of 30 rpm for 1 min. Subsequently, the coated Bio-skin plate was soaked into water for another 1 min and washed by de-ionized water. After naturally drying at around 25° C. for 2 hours, the L, a, and b of the Bio-skin plate were measured again by Digieye Imaging System and the ITA value of the Bio-skin plate (ITA$_2$) was calculated. The surface density after wash-off/abrasion experiment (SD$_2$) was obtained according to the calibration curve.

The deposition ratio after wash-off/abrasion experiment was calculated by:

Deposition ratio=(SD$_2$/SD$_1$)×100%.

Measurement of Contact Angle and Water Soaking Test

The contact angles of five film-forming polymers including Dow Corning™ MQ-1640 Flake Resin, Dow Corning™ MQ-1600 Solid Resin, Dow Corning™ 670 Fluid from Dow Corning, Avalure™ UR450 from Lubrizol, Lexorez™ 100 from Index were conducted. Dow Corning™ MQ-1600 Solid Resin and Dow Corning™ 670 Fluid were dispersed into dimethicone with a polymer to solvent weight ratio of 1:9. The other three polymers were dispersed into ethanol with a polymer to solvent weight ratio of 1:9.

0.2 ml of film-forming polymer dispersions were dripped evenly onto an ordinary glass sides (about 2 cm×8 cm). After the solvents evaporated, uniform films were formed. Drop shape analysis system 100 (DSA 100, Krüss) was used to measure contact angle using deionised water drops of around 5 μL applied to five different points of each film. The contact angle averaged over all 5 drops.

The contact angles of Dow Corning™ MQ-1640 Flake Resin, Dow Corning™ MQ-1600 Solid Resin, Dow Corning™ 670, Avalure™ UR450, and Lexorez™ 100 were 107°, 116°, 114°, 66°, and 28° respectively.

Then, these glass slides coated with polymer films were immersed fully into water for 30 minutes. After that the glass slides were taken out from water and dried. The contact angles of these glass slides were measured again. It was surprisingly found that the contact angles of glass slides coated by Avalure™ UR450, and Lexorez™ 100 were decreased to less than 15°, indicating that the polymer film has been peeled off. In contrast, the contact angle of glass slides coated by Dow Corning™ MQ-1640 Flake Resin, Dow Corning™ MQ-1600 Solid Resin, and Dow Corning™ 670 remained almost the same, manifesting that the polymer films were adhered onto the glass slides firmly.

Example 1

This example demonstrates the inclusion of fatty acid into the compositions containing two film-forming polymers improved more on wash-off resistance than inclusion into the composition containing one film-forming polymer.

A series of cosmetic compositions were formulated as shown in Table 1 below.

The formulations were prepared by the following process. The optical particles were completely dispersed in the oil phase with other ingredients and the silicone resin and/or lipid (when present) mixed thoroughly. The resulting oil-based mixture was gradually added to the aqueous phase. The resulting mixture was emulsified under 9,000 rpm of shear stress for 10 minutes at 65° C. and gradually stirred and cooled to room temperature.

The deposition ratios of the samples were measured by following the Wash-off/abrasion resistance performance test.

TABLE 1

| Ingredient (wt %) | Samples | | | | | | | |
|---|---|---|---|---|---|---|---|---|
| | A | B | C | 1 | 2 | 3 | 4 | 5 |
| Water | Bal. | Bal. | Bal. | Bal. | Bal. | Bal. | Bal. | Bal. |
| Disodium EDTA | 0.10 | 0.10 | 0.10 | 0.10 | 0.10 | 0.10 | 0.10 | 0.10 |
| PEG-100 Stearate (Myij 59 P) | 1.85 | 1.85 | 1.85 | 1.85 | 1.85 | 1.85 | 1.85 | 1.85 |
| Glyceryl stearate | 1.00 | 1.00 | 1.00 | 1.00 | 1.00 | 1.00 | 1.00 | 1.00 |
| Caprylic/Capric Triglycerides | 3.00 | 3.00 | 3.00 | 3.00 | 3.00 | 3.00 | 3.00 | 3.00 |
| Aristoflex AVC UL | 1.00 | 1.00 | 1.00 | 1.00 | 1.00 | 1.00 | 1.00 | 1.00 |
| Cyclomethicone/DC 245 | 8.00 | 8.00 | 8.00 | 8.00 | 8.00 | 8.00 | 8.00 | 8.00 |
| Preservative | 0.20 | 0.20 | 0.20 | 0.20 | 0.20 | 0.20 | 0.20 | 0.20 |
| Titanium dioxide[a] | 1.00 | 1.00 | 1.00 | 1.00 | 1.00 | 1.00 | 1.00 | 1.00 |
| Silicone resin-1[b] | — | — | — | 3.00 | 3.00 | 3.00 | 3.00 | 3.00 |
| Silicone resin-2[c] | — | 3.00 | 3.00 | — | — | — | — | — |
| Stearic acid[d] | — | — | 1.00 | — | 0.50 | 1.00 | 2.00 | 3.00 |

[a]MT700Z, Titanium Dioxide (and) Stearic Acid (and) Aluminium Hydroxide supplied by TAYCA
[b]Dow Corning ™ MQ-1640 Flake Resin, a blend of MQ and T Propyl resins, supplied by Dow Corning.
[c]Dow Corning ™ MQ-1600 Solid Resin, a 100% active MQ resin, supplied by Dow Corning.
[d]Supplied by Emery Oleochemicals (M) Sdn. Bhd.

As can be seen in Table 2, when including stearic acid into composition containing silicone 1, the mixture of MQ and T silicone resin, the deposition ratios were increased about 8 to 12. In contrast, when including stearic into composition containing silicone 2, the deposition ratio was increased only 5.4. It was surprisingly found that the fatty acid can improve the deposition ratio of composition containing silicone-1 more than that of the composition containing silicone-2.

TABLE 2

| Sample | Silicone resin-1 (wt %) | Silicone resin-2 (wt %) | Stearic acid (wt %) | Deposition Ratio (%) |
|---|---|---|---|---|
| B | 0 | 3.00 | 0 | 30.1 ± 2.6 |
| C | 0 | 3.00 | 1.00 | 35.5 ± 2.0 |
| 1 | 3.00 | 0 | 0 | 61.5 ± 3.1 |
| 2 | 3.00 | 0 | 0.50 | 69.3 ± 1.6 |
| 3 | 3.00 | 0 | 1.00 | 73.8 ± 2.1 |
| 4 | 3.00 | 0 | 2.00 | 85.6 ± 6.3 |
| 5 | 3.00 | 0 | 3.00 | 72.5 ± 2.3 |

Example 2

This example demonstrates the inclusion of different fatty acids into the compositions with two film-forming polymers improved the wash-off resistance of the compositions.

The formulations in Table 3 were prepared and the deposition ratios were tested by the following similar procedures as described in Example 1.

TABLE 3

| Ingredient (wt %) | 6 | 7 | 8 | 9 | 10 |
|---|---|---|---|---|---|
| Water | Bal. | Bal. | Bal. | Bal. | Bal. |
| Disodium EDTA | 0.10 | 0.10 | 0.10 | 0.10 | 0.10 |
| PEG-100 Stearate (Myij 59 P) | 1.85 | 1.85 | 1.85 | 1.85 | 1.85 |
| Glyceryl stearate | 1.00 | 1.00 | 1.00 | 1.00 | 1.00 |
| Caprylic/Capric Triglycerides | 3.00 | 3.00 | 3.00 | 3.00 | 3.00 |
| Aristoflex AVC UL | 1.00 | 1.00 | 1.00 | 1.00 | 1.00 |
| Cyclomethicone/DC 245 | 8.00 | 8.00 | 8.00 | 8.00 | 8.00 |
| Preservative | 0.20 | 0.20 | 0.20 | 0.20 | 0.20 |
| Titanium dioxide [a] | 1.00 | 1.00 | 1.00 | 1.00 | 1.00 |
| Silicone resin-1 [b] | 3.00 | 3.00 | 3.00 | 3.00 | 3.00 |
| Lauric acid [c] | 1.00 | — | — | — | — |
| Myristic acid [c] | — | 1.00 | — | — | — |
| Palmitic acid [c] | — | — | 1.00 | — | — |
| Oleic acid [c] | — | — | — | 1.00 | — |
| 12-hydroxy stearic acid [d] | — | — | — | — | 1.00 |
| Deposition Ratio (%) | 71.6 ± 2.5 | 72.1 ± 3.3 | 72.6 ± 2.9 | 71.6 ± 1.9 | 68.3 ± 3.0 |

[a] MT700Z, Titanium Dioxide (and) Stearic Acid (and) Aluminium Hydroxide supplied by TAYCA
[b] Dow Corning™ MQ-1640 Flake Resin, a blend of MQ and T Propyl resins, supplied by Dow Corning.
[c] Supplied by Emery Oleochemicals (M) Sdn. Bhd.
[d] Supplied by Vertellus Performance Materials Inc.

As shown in the last row of Table 3, the deposition ratios of composition containing both film-forming polymer and different fatty acids had been increased by comparing with that of composition containing film-forming polymer merely. It was manifested that the incorporation of different fatty acids improved wash-off resistance and therefore long-lasting whitening. It was also surprisingly found that the fatty acid without substitution improved wash-off resistance more than the fatty acid with a degree of substitution.

Example 3

This example demonstrates the inclusion of wax into the composition containing two film-forming polymers improved more on wash-off resistance than inclusion into the composition containing one film-forming polymer.

The formulations in Table 4 were prepared and the deposition ratios were tested by the following similar procedures as described in Example 1.

TABLE 4

| Ingredient (wt %) | E | F | 11 | 12 |
|---|---|---|---|---|
| Water | Bal. | Bal. | Bal. | Bal. |
| Disodium EDTA | 0.10 | 0.10 | 0.10 | 0.10 |
| PEG-100 Stearate (Myij 59 P) | 1.85 | 1.85 | 1.85 | 1.85 |
| Glyceryl stearate | 1.00 | 1.00 | 1.00 | 1.00 |
| Caprylic/Capric Triglycerides | 3.00 | 3.00 | 3.00 | 3.00 |
| Aristoflex AVC UL | 1.00 | 1.00 | 1.00 | 1.00 |
| Cyclomethicone/DC 245 | 8.00 | 8.00 | 8.00 | 8.00 |
| Preservative | 0.20 | 0.20 | 0.20 | 0.20 |
| Titanium dioxide [a] | 1.00 | 1.00 | 1.00 | 1.00 |
| Silicone resin-1 [b] | — | — | 3.00 | 3.00 |
| Silicone resin-2 [c] | — | 3.00 | — | — |
| Beeswax [d] | 1.00 | 1.00 | 1.00 | — |
| Petroleum jelly [e] | — | — | — | 1.00 |
| Deposition Ratio | 7.2 ± 0.9 | 50.9 ± 0.5 | 87.7 ± 3.0 | 76.6 ± 2.5 |

[a] MT700Z, Titanium Dioxide (and) Stearic Acid (and) Aluminium Hydroxide supplied by TAYCA
[b] Dow Corning™ MQ-1640 Flake Resin, a blend of MQ and T Propyl resins, supplied by Dow Corning.
[c] Dow Corning™ MQ-1600 Solid Resin, a 100% active MQ resin, supplied by Dow Corning.
[d] Wax#100, White Beeswax, supplied by Koster Keunen Inc.
[e] MERKUR™ 620, supplied by Sasol.

As can be seen in last row of Table 4, by adding wax into composition containing one film-forming polymer, the deposition ratio was increased 20.8 (Sample F vs. Sample C). In contrast, by adding wax into composition containing two film-forming polymers, the deposition ratio was increased 26.2. It was surprisingly found that by incorporating wax the deposition ratio of composition containing silicone-1 was unexpectedly increased more than composition containing silicone-2. It was manifested that the addition of wax into composition comprising two film-forming polymers enhanced the wash-off resistance, rub resistance more than into composition containing one film-forming polymer.

Example 4

The following examples are also within the present invention.

TABLE 5

| Ingredient (wt %) | 13 | 14 | 15 | 16 | 17 |
|---|---|---|---|---|---|
| Water | Bal. | Bal. | Bal. | Bal. | Bal. |
| Disodium EDTA | 0.10 | 0.10 | 0.10 | 0.10 | 0.10 |
| PEG-100 Stearate (Myij 59 P) | 1.85 | 1.85 | 1.85 | 1.85 | 1.85 |
| Glyceryl stearate | 1.00 | 1.00 | 1.00 | 1.00 | 1.00 |
| Caprylic/Capric Triglycerides | 3.00 | 3.00 | 3.00 | 3.00 | 3.00 |
| Aristoflex AVC UL | 1.00 | 1.00 | 1.00 | 1.00 | 1.00 |
| Cyclomethicone/DC 245 | 8.00 | 8.00 | 8.00 | 8.00 | 8.00 |
| Preservative | 0.20 | 0.20 | 0.20 | 0.20 | 0.20 |
| Titanium dioxide [a] | 1.00 | 1.00 | 0.90 | 0.90 | 1.00 |
| Silicone resin [b] | 3.00 | 1.50 | 3.00 | 3.00 | 3.00 |
| Dimethiconol [c] | — | 1.50 | 1.00 | — | — |
| amodimethicone [d] | — | — | — | 1.00 | — |
| Cholesterol [e] | — | — | — | — | 1.00 |

[a] MT700Z, Titanium Dioxide (and) Stearic Acid (and) Aluminium Hydroxide supplied by TAYCA
[b] Dow Corning™ MQ-1640 Flake Resin, a blend of MQ and T Propyl resins, supplied by Dow Corning.
[c] Dow Corning™ 1501 (15% active), Cyclopentasiloxane (and) Dimethiconol supplied by Dow Corning.
[d] Dow Corning™ 8500 conditioning agent, bis (C13-15 alkoxy) PG amodimethicone, supplied by Dow corning.
[e] Cholesterol NF supplied by RITA Corporation.

The invention claimed is:
1. A cosmetic composition comprising:
   a) first film-forming polymer having a contact angle of at least 85°, the first film-forming polymer comprising an MQ silicone resin;

b) a second film-forming polymer having a contact angle of at least 85°, the second film-forming polymer comprising a T silicone resin;
c) a lipid having a melting point of at least 5° C.;
d) optical particle; and
e) at least 20% of water by weight of the composition
wherein the first and second film-forming polymers and the lipid are at a weight ratio of 1:1 to 5:1.

2. The composition according to claim 1 wherein the first film-forming polymer is an MQ silicone resin.

3. The composition according to claim 1 wherein the second film-forming polymer is a T silicone resin and comprises polypropyl silsesquioxane.

4. The composition according to claim 1 wherein the total amounts of film-forming polymers is from 0.01 to 20% by weight of the composition.

5. The composition according to claim 1 wherein the weight ratio of the first film-forming polymer to the second film-forming polymer is from 20:1 to 1:10.

6. The composition according to claim 1 wherein the lipid comprises fatty acid, soap, fatty alcohol, fatty ester, wax, steroid, ceramide or a mixture thereof.

7. The composition according to claim 6 wherein the lipid comprises fatty acid and further wherein the fatty acid comprises stearic, lauric, palmitic, isostearic, myristic acid, or a mixture thereof.

8. The composition according to claim 7 wherein the amount of fatty acid is from 0.1 to 10% by weight of the composition.

9. The composition according to claim 6 wherein the lipid comprises a wax.

10. The composition according to claim 9 wherein amount of wax is from 0.1 to 10% by weight of the composition.

11. The composition according to claim 6 wherein the lipid comprises a steroid.

12. The composition according to claim 11 wherein the amount of steroid is from 0.1 to 10% by weight of the composition.

13. The composition according to claim 1 wherein the lipid is present in amount of 0.01 to 20% by weight of the composition.

14. The composition according to claim 1 wherein the composition further comprises sunscreen, preservative, is a cream and the weight ratio of the first and second film-forming polymers to lipid is 2:1 to 4:1.

15. The composition according to claim 1 wherein the optical particle is present in amount of 0.05 to 5% by weight of the composition.

16. The composition according to claim 1 wherein the optical particle comprises titanium dioxide, zinc oxide, zirconium oxide, mica, iron oxide or a combination thereof.

17. The composition according to claim 1 wherein the weight ratio of the lipid to the optical particle is from 5:1 to 1:5.

18. The composition according to claim 1 wherein the composition comprises at least 40% of water by weight of the composition.

19. The composition according to claim 1 wherein the lipid has a melting point of at least 35° C.

20. A method for improving skin characteristic comprising the step of topically applying to skin the composition of claim 1 wherein the composition is a skin care composition.

* * * * *